United States Patent [19]

Andersen et al.

[11] Patent Number: 5,279,293

[45] Date of Patent: Jan. 18, 1994

[54] IMPLANTABLE DEFIBRILLATOR WITH FIBRILLATION-INDUCING CAPABILITY AND METHOD FOR INDUCING FIBRILLATION

[75] Inventors: Hans Andersen, Voellingby; Martin Obel, Danderyd; Lars Wallen, Sundbyberg, all of Sweden

[73] Assignee: Siemens Aktiengesellschaft, Munich, Fed. Rep. of Germany

[21] Appl. No.: 861,150

[22] Filed: Mar. 31, 1992

[30] Foreign Application Priority Data

Apr. 9, 1991 [DE] Fed. Rep. of Germany ....... 4111478

[51] Int. Cl.⁵ .............................................. A61N 1/00
[52] U.S. Cl. .......................................... 607/5; 607/2
[58] Field of Search ....... 128/419 D, 419 R, 419 PG

[56] References Cited

U.S. PATENT DOCUMENTS

| 3,602,229 | 8/1971 | Jaros et al. ..................... 128/419 D |
| 4,300,567 | 11/1981 | Kolenik et al. |
| 4,494,544 | 1/1985 | Lambert |
| 4,996,984 | 5/1991 | Sweeney ......................... 128/419 D |
| 5,105,809 | 4/1992 | Bach, Jr. et al. ................ 128/419 D |
| 5,111,816 | 5/1992 | Pless et al. .................... 128/419 D X |
| 5,129,392 | 7/1992 | Bardy et al. ................... 128/419 R X |

FOREIGN PATENT DOCUMENTS

| 0392099 | 10/1990 | European Pat. Off. |
| 1927667 | 12/1970 | Fed. Rep. of Germany |
| 2811325 | 9/1979 | Fed. Rep. of Germany |
| 3919498 | 1/1990 | Fed. Rep. of Germany |
| 3910741 | 10/1990 | Fed. Rep. of Germany |
| 4030306 | 4/1991 | Fed. Rep. of Germany |

OTHER PUBLICATIONS

Járos et al., "New Approaches to Fibrillation and Defibrillation of the Heart," S. A. Medical Journal, 22 Jan. 1972, pp. 63–67.

Starmer et al., "Current Density and Electrically Induced Fibrillation," Medical Instrumentation, vol. 7, No. 1, Jan.–Feb. 1973.

Levy et al., "Cardiac Fibrillation-Defibrillation: Use of Electrical Current in Conversion of Cardiac Rhythm-Methods and Results", Am. Journal of Med. Elec. Oct.–Dec. '64.

"Ventricular Fibrillation Threshold in the Dog Determined with Defibrillating Paddles," Ruiz et al., Med. & Biol. Eng. & Comput., May 1985, pp. 281–284.

Primary Examiner—Francis Jaworski
Assistant Examiner—Jeffrey R. Jastrzab
Attorney, Agent, or Firm—Hill, Steadman & Simpson

[57] ABSTRACT

An implantable defibrillator has a capacitor which, through a controllable switch arrangement, can either be connected to a voltage source for charging the capacitor, or connected across electrodes placed at the heart for delivering a defibrillation pulse. To calculate the minimum pulse energy required for successful defibrillation, ventricular fibrillation is first induced, so that a plurality of defibrillation attempts, with energy increasing from attempt-to-attempt can be undertaken until successful defibrillation occurs. For inducing ventricular fibrillation, the capacitor of the implantable defibrillator is connected to the voltage source until a prescribed charging voltage, which is significantly below the voltage necessary for defibrillation, is reached, and subsequently, the capacitor is disconnected from the voltage source during brief time spans at intervals within the framework of a sequence and is connected during those time spans to the electrodes. Between the time spans, the capacitor is again charged.

12 Claims, 1 Drawing Sheet

IMPLANTABLE DEFIBRILLATOR WITH FIBRILLATION-INDUCING CAPABILITY AND METHOD FOR INDUCING FIBRILLATION

BACKGROUND OF THE INVENTION

1. Field of the Invention

The present invention is directed to an implantable defibrillator of the type having a capacitor which is connectable via a controllable switch arrangement to a voltage source for charging or to electrodes placed at the heart for delivery of defibrillation pulses thereto, and to a method for inducing fibrillation using such a defibrillator.

2. Description of the Prior Art

In known implantable defibrillators, a capacitor connected within the implantable defibrillator housing or capsule, is charged to a high voltage via a voltage source, also in the housing, and is subsequently discharged through electrodes arranged at the heart and via the heart tissue lying between the electrodes, upon the detection of ventricular fibrillation. A controllable switch arrangement normally connects the capacitor across a voltage source for charging the capacitor, and alternatively connects the capacitor across the electrodes when defibrillation is necessary. When the current flowing across the heart has sufficient energy, ventricular fibrillation is thereby terminated.

In order to identify the minimum amount of energy which is sufficient to achieve a successful defibrillation, it is known to induce ventricular fibrillation artificially, and subsequently to implement a series of defibrillation attempts with increasing energy until the ventricular fibrillation is successfully terminated. For example, ventricular fibrillation can be induced by externally charging the patient with a 50 Hz alternating current from an external generator. It is possible to artificially produce ventricular fibrillation by generating a suitable stimulation pulse sequence by means of a heart pacemaker, which may be implanted either separately from the implantable defibrillator, or in combination with the defibrillator in a common housing.

SUMMARY OF THE INVENTION

It is an object of the present invention to provide an implantable defibrillator of the type having a capacitor connectable via a controllable switch arrangement either to a voltage source for charging, or to electrodes for delivery of pulses to the heart, by means of which fibrillation can be artificially induced in the heart in a simple manner.

It is a further object of the present invention to provide a method for artificially inducing fibrillation using an implantable defibrillator of this type.

The above objects are achieved in accordance with the principles of the present invention in a defibrillator of the type described above, including means for operating the switch arrangement for connecting the capacitor across the voltage source until a prescribed charging voltage is reached, which is significantly below the voltage provided for defibrillation, and thereafter, once the charging voltage is reached, for disconnecting the capacitor from the voltage source and connecting the capacitors across the electrodes during a series of brief time spans, which follow each other at intervals within the frame work of a sequence. During the intervals between the time spans, the capacitor is again connected to the voltage source for charging. Ventricular fibrillation can thus be produced using the implantable defibrillator, without the necessity of providing a pulse generator specifically for that purpose, and also without the necessity of providing special electrodes. Instead, the defibrillator disclosed herein generates the pulse sequence required for inducing ventricular fibrillation with the components which are already provided in the defibrillator for defibrillation purposes.

Moreover, because the electrodes, normally used to effect defibrillation are usually large-area electrodes, the pulses which are delivered for the purpose of inducing fibrillation can be limited to a relatively low value, so that damage to the heart tissue is avoided while still reliably inducing ventricular fibrillation. For example, the amplitude of the fibrillation-inducing pulses can be approximately 23 volts, which is significantly below the voltage normally provided for defibrillation. The duration of the time spans which define the pulse duration is preferably on the order of magnitude of 8 ms, and the duration of the interval between pulses is preferably on the order of magnitude of 25 ms.

The voltage amplitude of the pulses can be set by directly measuring the voltage across the capacitor to identify when the prescribed charging voltage is reached.

Alternatively, in a preferred embodiment, the capacitor is charged with a prescribed charging current by the voltage source, and the prescribed charging voltage is defined by the expiration of a given time after the beginning of the charging event.

In a preferred embodiment of the invention, the charging current for the capacitor is variable, at least for duration of the fibrillation-inducing sequence, so that pulse sequences having a steady increase or decrease in the pulse height (amplitude) of the individual pulses can be generated.

DESCRIPTION OF THE PREFERRED EMBODIMENTS

Figure 1:
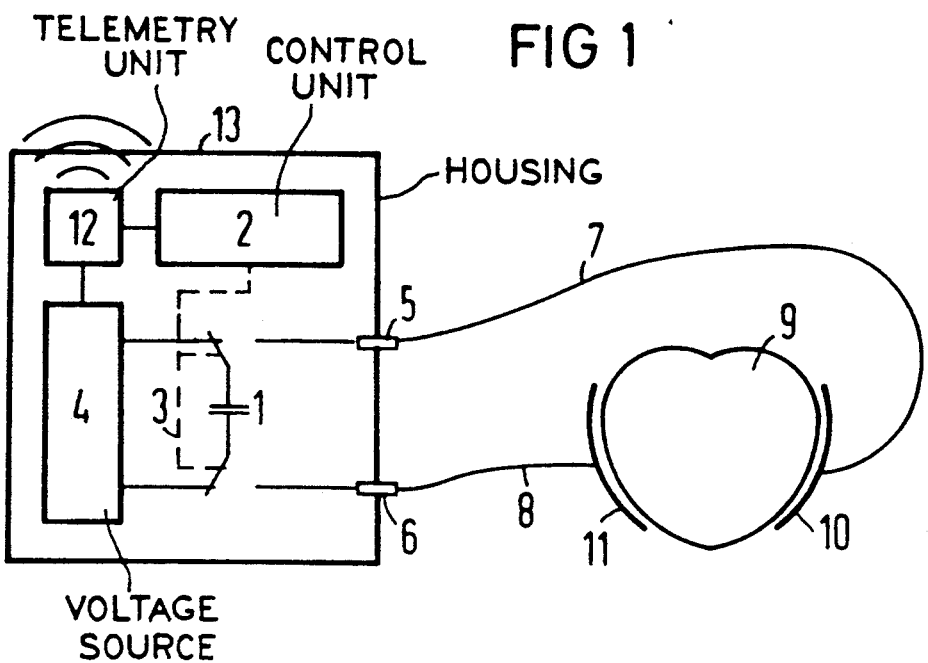
FIG. 1 is a block circuit diagram of a preferred exemplary embodiment of a defibrillator constructed in accordance with the principles of the present invention.

An exemplary embodiment of an implantable defibrillator is shown in FIG. 1, having a capacitor 1 connectable either to a voltage source 4 or to terminals 5 and 6. The capacitor is connected across either the voltage source 4 or the terminals 4 and 5 by means of a switch arrangement 3 operated by a control unit 2. Respective implantable leads 7 and 8 are connected to the terminals 5 and 6, the leads 7 and 8 respectively terminating in electrodes 10 and 11 which are arranged directly at the heart 9. The capacitor 1, the control unit 2, the switch arrangement 3, the voltage source 4 and a telemetry unit 12 are contained in an implantable capsule housing 13. The telemetry unit 12 is connected to the control unit 2 and to the voltage source 4 for communication with an external programming device (not shown) in a known manner. The electrode terminals 5 and 6 are feedthroughs which extend through the wall of the capsule housing 13, while still permitting the interior of the capsule housing 13 to remain hermetically sealed.

When spontaneous fibrillation of the heart 9 is detected by any of a number of known techniques, the capacitor 1 is connected to the voltage source 4 via the controllable switch arrangement 3 and is charged to a high voltage. The capacitor 1 is subsequently connected by the controllable switch arrangement 3 to the electrode terminals 5 and 6, and the capacitor 1 is discharged through the electrodes 10 and 11 and the heart tissue lying therebetween, and thus effects defibrillation if the discharge current has a sufficient amount of energy. It is therefore necessary in conjunction with the implantation of the defibrillator to identify the lowest amount of energy which will suffice for successful defibrillation. To that end, ventricular fibrillation is artificially induced in the heart 9, and a plurality of defibrillation attempts are subsequently undertaken, each attempt being with a higher energy level until successful defibrillation of the heart 9 occurs. Inducing ventricular fibrillation using the defibrillator constructed in accordance with the principles of the present invention is described in detail below with reference to FIG. 2.

Figure 2:
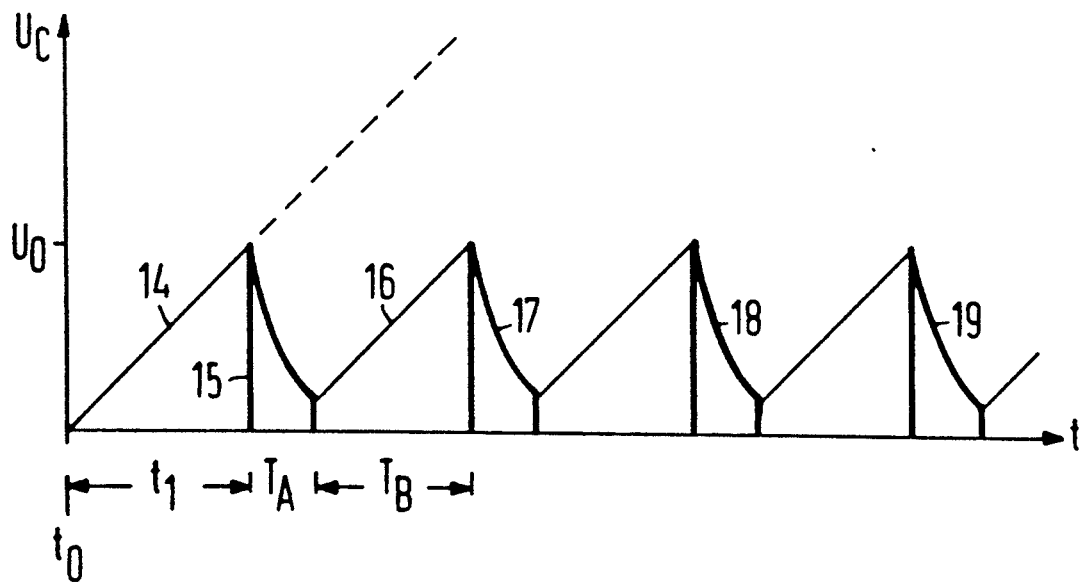
FIG. 2 is a graph showing an example of the pulse sequence generated by the defibrillator shown in FIG. 1 for inducing ventricular fibrillation.

As shown in FIG. 2, the capacitor 1 is connected at a time $t_O$, to the voltage source 4 via the controllable switch arrangement 3, and is charged with the voltage curve referenced 14. The voltage across the capacitor 1, i.e., the charging voltage, is referenced $U_c$. Upon reaching a prescribed charging voltage $U_O$ the capacitor 1 is disconnected from the voltage source for by the controllable switch arrangement 3. The prescribed charging voltage $U_O$ can be identified either by measuring the voltage $U_c$ across the capacitor 1 or, in the case of a given charging current, by the expiration of a prescribed time $t_1$ following the beginning of the charging event at $t_0$.

When the prescribed charging voltage $V_o$ is reached, the controllable switch arrangement 3 is operated to connect the capacitor 1 across the electrode terminals 5 and 6 for a brief time span $T_A$. During this time span $T_A$, the capacitor 1 is discharged so as to generate an output pulse 15 across the heart tissue lying between the electrodes 10 and 11. At the end of the time span $T_A$, the capacitor 1 is again connected by the switch arrangement 3 to the voltage source 4, and is charged in accord with the voltage curve referenced 16 during an interval $T_B$. At the end of the interval $T_B$, the capacitor 1 is again discharged across the heart tissue 9 for a time span $T_A$. This procedure is repeated over a sequence consisting of a plurality of pulses 15, 17, 18 and 19, resulting in the artificial inducement of ventricular fibrillation. By varying the charging current, i.e., by varying the slope of the voltage curves 14 and 16 in FIG. 2, sequences having continuously rising or decreasing pulse heights can be generated without altering the interval $T_B$.

Although modifications and changes may be suggested by those skilled in the art it is the intention of the inventors to embody within the patent warranted hereon all changes and modifications as reasonably and properly come within the scope of their contribution to the art.

We claim as our invention:

1. An implantable defibrillator comprising:
   a capacitor;
   a voltage source;
   electrode means for delivering electrical energy in vivo to a heart;
   switch means for connecting said capacitor either across said voltage source or across said electrode means; and
   control means for operating said switch means to connect said capacitor across said voltage source until said capacitor is charged to a voltage for defibrillation of said heart and, at selected times, to artificially induce ventricular fibrillation in said heart by connecting said capacitor across said voltage source until said capacitor is charged to a prescribed charging voltage which is significantly below said voltage for defibrillation and thereafter disconnecting said capacitor from said voltage source and connecting said capacitor across said electrode means during a plurality of spaced time intervals in a sequence.

2. An implantable defibrillator as claimed in claim 1 wherein said control means operates said switch means connecting said capacitor across said electrode means for time intervals of approximately 8 ms.

3. An implantable defibrillator as claimed in claim 1 wherein said control means operates said switch means connecting said capacitor across said voltage source between said time intervals for respective durations of approximately 25 ms.

4. An implantable defibrillator as claimed in claim 1 further comprising means for directly measuring the voltage across said capacitor for identifying when said prescribed charging voltage is reached.

5. An implantable defibrillator as claimed in claim 1 wherein said capacitor is charged by said voltage source with a prescribed charging current, and further comprising means for defining when said prescribed charging voltage is reached by measuring the expiration of a prescribed time following a beginning of charging of said capacitor.

6. An implantable defibrillator as claimed in claim 5 further comprising means for varying said charging current at least during said sequence.

7. A method for in vivo delivery of electrical energy to the heart, said method comprising the steps of:
   implanting a defibrillator and electrodes in a patient, said defibrillator containing a voltage source and a capacitor;
   disposing said electrodes relative to said heart for in vivo delivery of electrical energy from said defibrillator to said heart;
   connecting said capacitor across said voltage source until said capacitor reaches a voltage for defibrillation of said heart and, in the event of fibrillation discharging said capacitor across said electrodes;
   connecting said capacitor to a voltage source until said capacitor reaches a prescribed charging voltage which is significantly below said voltage for defibrillation for inducing fibrillation in said heart at selected times;
   after reaching said prescribed charging voltage, disconnecting said capacitor from said voltage source and connecting said capacitor across said electrodes for a plurality of spaced time intervals in a sequence; and
   re-connecting said capacitor across said voltage source between said time intervals for charging said capacitor.

8. A method as claimed in claim 7 wherein the step of connecting said capacitor across said electrodes for a plurality of spaced time intervals is further defined by connecting said capacitor across said electrodes for a plurality of spaced time intervals each lasting approximately 8 ms.

9. A method as claimed in claim 7 wherein the step of re-connecting said capacitor across said voltage source for charging said capacitor between said time intervals is further defined by re-connecting said capacitor across said voltage source for a time lasting approximately 25 ms between each of said time intervals.

10. A method as claimed in claim 7 comprising the additional step of:
   directly measuring the voltage across said capacitor for identifying when said prescribed charging voltage is reached.

11. A method as claimed in claim 7 wherein the step of connecting said capacitor across said voltage source for charging said capacitor is further defined by charging said capacitor with a prescribed charging current, and comprising the additional step of measuring the expiration of prescribed time following a beginning of charging of said capacitor for defining when said prescribed charging voltage is reached.

12. A method as claimed in claim 11 comprising the additional step of varying said charging current for said capacitor at least during said sequence.

* * * * *